(12) United States Patent
Yu et al.

(10) Patent No.: US 11,937,920 B2
(45) Date of Patent: Mar. 26, 2024

(54) CLOUD BIG DATA-BASED INTELLIGENT REAL-TIME DYNAMIC BLOOD GLUCOSE MONITORING SYSTEM AND METHOD

(71) Applicant: MICROTECH MEDICAL (HANGZHOU) CO., LTD., Hangzhou (CN)

(72) Inventors: Fei Yu, Hangzhou (CN); Zhiyan Chen, Hangzhou (CN)

(73) Assignee: MICROTECH MEDICAL (HANGZHOU) CO., LTD., Hangzhou (CN)

( * ) Notice: Subject to any disclaimer, the term of this patent is extended or adjusted under 35 U.S.C. 154(b) by 765 days.

(21) Appl. No.: 16/969,112

(22) PCT Filed: Oct. 8, 2018

(86) PCT No.: PCT/CN2018/109283
§ 371 (c)(1),
(2) Date: Aug. 11, 2020

(87) PCT Pub. No.: WO2019/072142
PCT Pub. Date: Apr. 18, 2019

(65) Prior Publication Data
US 2023/0240565 A1    Aug. 3, 2023

(30) Foreign Application Priority Data
Oct. 12, 2017  (CN) .................. 201710947227.0

(51) Int. Cl.
*A61B 5/145*    (2006.01)
*A61B 5/00*    (2006.01)
(Continued)

(52) U.S. Cl.
CPC ........ *A61B 5/14532* (2013.01); *A61B 5/0022* (2013.01); *A61B 5/1473* (2013.01);
(Continued)

(58) Field of Classification Search
CPC . A61B 5/14532; A61B 5/0022; A61B 5/1473; A61B 5/6826; A61B 5/7246;
(Continued)

(56) References Cited

U.S. PATENT DOCUMENTS

| 2017/0000391 A1 | 1/2017 | Wasson et al. |
| 2017/0071513 A1 | 3/2017 | Hoss et al. |
| 2017/0074757 A1* | 3/2017 | Garcia ............... A61B 5/14532 |

FOREIGN PATENT DOCUMENTS

| CN | 104736057 A | 6/2015 |
| CN | 106456065 A | 2/2017 |

(Continued)

*Primary Examiner* — Eric F Winakur
*Assistant Examiner* — Abid A Mustansir
(74) *Attorney, Agent, or Firm* — Bayramoglu Law Offices LLC (57) ABSTRACT

Intelligent real-time blood glucose monitoring system and method based on cloud big data is disclosed. The system includes an implantable dynamic glucose sensor, a smart phone, a blood glucose monitoring software application installed on the smart phone, a finger blood glucose meter, and a big data cloud server. By processing historical blood glucose measurement data of a user stored in the cloud, the monitoring system effectively corrects and influences signal differences produced by individual users so as to ensure the validity and accuracy of measurement signals during sensor operation.

7 Claims, 2 Drawing Sheets

(51) Int. Cl.
*A61B 5/1473* (2006.01)
*G16H 10/60* (2018.01)
*G16H 40/67* (2018.01)
*H04M 1/72412* (2021.01)

(52) U.S. Cl.
CPC .......... *A61B 5/6826* (2013.01); *A61B 5/7246* (2013.01); *A61B 5/7264* (2013.01); *G16H 10/60* (2018.01); *G16H 40/67* (2018.01); *A61B 2560/0285* (2013.01); *H04M 1/72412* (2021.01)

(58) Field of Classification Search
CPC .......... A61B 5/7264; A61B 2560/0285; A61B 5/0004; A61B 5/14503; G16H 10/60; G16H 40/67; H04M 1/72412; H04L 67/12; H04L 67/10; G08C 17/02
See application file for complete search history.

(56) References Cited

FOREIGN PATENT DOCUMENTS

| | | |
|---|---|---|
| CN | 106535762 A | 3/2017 |
| CN | 107135644 A | 9/2017 |
| WO | 2017116503 A1 | 7/2017 |

* cited by examiner

CLOUD BIG DATA-BASED INTELLIGENT REAL-TIME DYNAMIC BLOOD GLUCOSE MONITORING SYSTEM AND METHOD

CROSS REFERENCE TO THE RELATED APPLICATIONS

This application is the national phase entry of International Application No. PCT/CN2018/109283, filed on Oct. 8, 2018, which is based upon and claims priority to Chinese Patent Application No. 201710947227.0, filed on Oct. 12, 2017, the entire contents of which are incorporated herein by reference.

TECHNICAL FIELD

The invention relates to the technical field of intelligent medical devices, and in particular, to an intelligent real-time dynamic blood glucose monitoring system and method based on cloud big data.

BACKGROUND

There are various types of biosensors for sensing a variety of analytes in the market. The most widely used and most common biosensor is the amperometric glucose sensor, which is critical for successfully controlling the glucose level in patients having diabetes mellitus. Currently, implantable glucose sensors are the most advanced continuous human blood glucose monitoring system in the world. A sensor probe is implanted into the dermal tissue to monitor the glucose content in the subcutaneous interstitial fluid and the human blood glucose value calculated.

The signal obtained by the amperometric glucose sensor is easily affected by chemical differences of individuals, their lifestyle habits and physical condition. These include, but are not limited to, differences in glucose content between the subcutaneous tissue fluid and capillary and venous blood, the time delay between the fluctuation change of blood glucose and the change of glucose content in the subcutaneous interstitial fluid, rejection of the sensor by the body resulting in the formation of an impermeable sheath-like protein layer covering the sensor, and the local skin discomfort and allergic reactions caused by the sensor over time. As a result, the amperometric electrochemical sensor cannot distinguish the signal source of its working electrode, which substantially impacts the accuracy of glucose monitoring and the health and well-being of the individual.

For this reason, the amperometric electrochemical sensor needs a set of solutions that can correct the signal. At present, the general method is to remind the user to compare the signal value measured by the sensor with the finger blood glucose value measured by the blood glucose meter on a regular basis, so as to manually recalibrate the sensor signal. Adjustment of the correlation between the current signal and the concentration of analyte must also be done manually to ensure accuracy. This increases the difficulty and complexity of use of the sensor, which causes user inconvenience, frustration and unacceptable risk to the user's health.

SUMMARY

The purpose of the invention is to provide an intelligent real-time dynamic blood glucose monitoring system and method based on cloud big data, so as to solve the shortcomings of the prior art.

The invention includes the following technical scheme.

An intelligent real-time dynamic blood glucose monitoring system based on cloud big data includes an implantable dynamic glucose sensor, a smart phone and a blood glucose monitoring application software installed on the smart phone, a finger blood glucose meter and a cloud big data server.

The implantable dynamic glucose sensor includes a replaceable sensor probe, a reusable signal collector and a signal transmitter with an electrochemical impedance spectrum measurement function, wherein the output of electrochemical impedance spectrum measurement includes the impedance value and phase of the impedance or the real and imaginary parts of the impedance. The signal transmitter of implantable dynamic glucose sensor is connected with the smart phone through wireless connection and transmits data with blood glucose monitoring application software.

The smart phone and the blood glucose monitoring application software installed on the smart phone have the functions of data transmission with the implantable dynamic glucose sensor and finger blood glucose meter by way of wireless communication technology, as well as data uploading and downloading through the smart phone data network or wireless network and cloud big data server.

The finger blood glucose meter collects blood samples from the user's fingertips for blood glucose measurement, and transmits data with the smart phone through wireless transmission.

The cloud big data server includes the functions of storing, updating, calculating and transmitting the user's personal information and historical data. The cloud big data server automatically corrects and calculates the parameter output data of the implantable dynamic glucose sensor and sends it to the smart phone terminal according to the user's historical data in the cloud database.

Preferably, the user's personal information and historical data stored in the cloud big data server include the user's name, gender, age, contact number, serial number and related information of the implantable dynamic glucose sensor, raw data Is of the implantable dynamic glucose sensor, signal-to-noise ratio SNR, blood glucose output value SG and the corresponding data measurement time and date Ts, the conversion coefficient CF and related parameters between the original data of the sensor and the blood glucose value, the blood glucose value BG measured by the users through the finger blood glucose meter and corresponding measurement time and date Tb, the electrochemical impedance data Z measured by the implantable dynamic glucose sensor and corresponding measurement time and date Tz.

Preferably, the conversion coefficient CF between the original data of the sensor stored and calculated in the cloud big data server and the blood glucose value at the time point t is calculated as follows $$CF(t) = \frac{CF0 + CFd \times t + \alpha \times CFcomp + \beta \times CFcal}{1 + \alpha + \beta}$$

wherein, the time point t is the zero point when the sensor is started. CF0 is the initial value of conversion coefficient. CFd is the change rate of conversion coefficient. CFcal is the correction compensation coefficient adjusted according to the blood glucose measurement value BG. CFcomp is the compensation conversion coefficient adjusted according to electrochemical impedance data Z; $\alpha$, $\beta$ are the weight coefficients of CFcomp and CFcal, with the value range of $0<\alpha<10$, $0<\beta<10$.

The cloud big data server calculates the corresponding CF related parameters through a regression algorithm according to the real-time updated data and historical data of specific users.

Preferably, CF0 and CFd are calculated as follows:

for each new user, the preset CF0 and CFd are used to calculate the sensor output blood glucose value:

$$SG=Is\times(CF0+CFd\times t)=Is\times CF0+(Is\times t)CFd$$

After the user has used the finger blood glucose meter to measure and compare their own blood glucose, the measured value of the blood glucose meter is collected through the smart phone and uploaded to the cloud big data server. The updated CF0 and CFd are calculated by regression equation. The specific method is as follows:

step A, extracting sample data: near each measurement time Tb of the finger blood glucose meter, screening out the dynamic glucose sensor data whose time interval |Tb −Ts| is less than the threshold value, and extracting the following data:

1. BG: measured data of finger blood glucose meter
2. SG: blood glucose calculation data of dynamic glucose sensor
3. Is: current data of dynamic glucose sensor
4. Ts: time stamp data of dynamic glucose sensor
5. T0s: start time stamp data of dynamic glucose sensor selecting the data with |SG−BG| less than the threshold value as valid samples to form a sample record package $[BG_n\ Is_n\ Ts_n\ T0s_n]$ for calculation;

using the data of the last three to six months for regression, and arranging the subscript number n of the historical data variable in reverse order of TS, that is, the closer to the current historical data, the smaller the subscript number, the data of dynamic glucose sensor can be from multiple sensor probes of the same model;

step B, establishing the sample matrix:

$$G=\begin{bmatrix}BG_1\\BG_2\\BG_3\\\vdots\\BG_n\end{bmatrix}\quad I=\begin{bmatrix}Is_1 & Is_1\times t_1\\Is_2 & Is_2\times t_2\\Is_3 & Is_3\times t_3\\\vdots & \vdots\\Is_n & Is_n\times t_n\end{bmatrix}$$

wherein, $t_n=Ts_n-T0s_n$;

step C, establishing the coefficient matrix:

$$C=\begin{bmatrix}CF0\\CFd\end{bmatrix};$$

step D, constructing the weight matrix:

$$W=\begin{bmatrix}w(Ts'_1) & & & & \\ & w(Ts'_2) & & & \\ & & w(Ts'_3) & & \\ & & & \ddots & \\ & & & & w(Ts'_n)\end{bmatrix}$$

wherein, $Ts'_n=T_{current}-Ts_n$, Tcurrent is the current time; $w(Ts'_n)$ is the weight coefficient of $Ts'_n$, so that the closer $Ts_n$ is to the current time, the greater the weight is;

step E, solving the overdetermined equation G=IC:

using the weighted least square method to solve the matrix equation $\hat{C}=(I^TWI)^{-1}I^TWG$;

step F, eliminating abnormal data: calculating the residual matrix $\varepsilon=G-I\hat{C}$, removing the data items with residuals greater than the threshold value, and then repeating step B to E of the regression algorithm to obtain updated values $\widehat{CF0}$ and $\widehat{CFd}$ of CF0 and CFd;

step G, finally, using the obtained $\widehat{CF0}$ and $\widehat{CFd}$ calculated by regression to correct the current set CF0 and CFd with a certain correction ratio γ as the conversion coefficient setting of the next dynamic glucose sensor:

$$CF0:=(1-\gamma)\times CF0+\gamma\times\widehat{CF0}$$

$$CFd:=(1-\gamma)\times CFd+\gamma\times\widehat{CFd}$$

the range of γ values is 0<γ<1.

Preferably, the calculation method of CFcal in the cloud big data server is as follows:

when the user uses the finger blood glucose meter to detect the blood glucose value BG, the BG, the sensor current signals Is and CFcal should conform to the following relationship with the smallest possible error:

$$BG=Is\times CFcal$$

step A, obtaining a new blood glucose value BG and measurement time Tb after each time the user uses the finger blood glucose meter for blood glucose detection, and selecting the dynamic glucose sensor data with time interval |Tb−Ts| less than the threshold value at the same time:

1. BG: measured data of finger blood glucose meter
2. SG: blood glucose calculation data of dynamic glucose sensor
3. Is: current data of dynamic glucose sensor
4. SNR: signal-to-noise ratio of dynamic glucose sensor current signal
5. Ts: time stamp data of dynamic glucose sensor selecting the data with |SG−BG| less than the threshold value as valid samples to form a sample record package $[BG_n\ Is_n\ SNR_n\ Ts_n]$ for calculation;

using the data in the latest period for regression, and arranging the subscript number n of the historical data variable in reverse order of Ts, that is, the closer to the current historical data, the smaller the subscript number. All the dynamic glucose sensor data must come from the same sensor probe; in which, the last period includes the last 5 days, the last 7 days, the last 10 days or the same period as the service life of the replaceable sensor probe;

step B, using regression algorithm to calculate the updated value CFcal' of CFcal:

$$CFcal'=\frac{\sum_{n=1}^{N}[Is_n\times BG_n\times SNR_n\times w(Ts'_n)]}{\sum_{n=1}^{N}[Is_n^2\times SNR_n\times w(Ts'_n)]}$$

wherein, $Ts'_n=T_{current}-Ts_n$, Tcurrent is the current time; $w(Ts'_n)$ is the weight coefficient of $Ts'_n$, so that the closer $Ts_n$ is to the current time, the greater the weight is.

Preferably, the calculation method of CFcomp is as follows:

CFcomp is a parameter associated with the measured value Z of electrochemical impedance by the correlation $F_{comp}(Z;\Omega)$:

$$CFcomp=F_{comp}(Z;\Omega)=\Omega a\times M(Z/Z0)+\Omega b$$

wherein, $\Omega$ is the built-in parameter array specific to the sensor $$\Omega = \begin{bmatrix} \Omega a \\ \Omega b \end{bmatrix}, M(Z/Z0)$$

is a function related to impedance data Z, and Z0 is the impedance value measured by the sensor in a controlled experimental environment;

when the user uses the finger blood glucose meter to detect the blood glucose value BG, the BG, the sensor current signal Is and CFcomp should conform to the following relationship with the smallest possible error:

$$BG = Is \times CFcomp$$
$$= Is \times M(Z/Z0) \times \Omega a + Is \times \Omega b$$

step A, near each measurement time Tb of the finger blood glucose meter, screening out the dynamic glucose sensor data whose time interval |Tb−Tz| is less than the threshold value, and extracting the following data:

1. BG: measured data of finger blood glucose meter
2. SG: blood glucose calculation data of dynamic glucose sensor
3. Is: current data of dynamic glucose sensor
4. Z: Impedance data of dynamic glucose sensor
5. Tz: time stamp data of dynamic glucose sensor selecting the data with |SG−BG| less than the threshold value as valid samples to form a sample record package $[BG_n\ IS_n\ Z_n\ Tz_n]$ for calculation;

using the data in the last three months for regression, and arranging the subscript number n of the historical data variable in reverse order of Tz, that is, the closer to the current historical data, the smaller the subscript number, the data of dynamic glucose sensor can come from multiple sensor probes of the same model;

step B, establishing sample matrix and weight matrix:

$$G = \begin{bmatrix} BG_1 \\ BG_2 \\ BG_3 \\ \vdots \\ BG_n \end{bmatrix}\ I = \begin{bmatrix} Is_1 \times M(z_1/z0) & Is_1 \\ Is_2 \times M(z_2/z0) & Is_2 \\ Is_3 \times M(z_3/z0) & Is_3 \\ \vdots & \vdots \\ Is_n \times M(z_n/z0) & Is_n \end{bmatrix}$$

$$W = \begin{bmatrix} w(Tz'_1) & & & & \\ & w(Tz'_2) & & & \\ & & w(Tz'_3) & & \\ & & & \ddots & \\ & & & & w(Tz'_n) \end{bmatrix}$$

wherein, $Tz'_n = Tcurrent - Tz_n$ the closer to the current time, the greater the weight is;

step C, solving the overdetermined equation $G = I\Omega$;

using the weighted least square method to solve the matrix equation $\hat{\Omega} = (I^T W I)^{-1} I^T W G$;

step D, eliminating abnormal data: calculating the residual matrix $\hat{\varepsilon} = G - I\hat{\Omega}$, removing the data items with residuals greater than the threshold value, and then repeating steps B to C to obtain the optimal solution $\hat{\Omega}$;

step E, using the obtained $\hat{\Omega}$ to correct the current set $\Omega$ with a certain correction ratio $\gamma$:

$$\Omega := (1-\gamma) \times \Omega + \gamma \times \hat{\Omega}$$

the range of $\gamma$ values is $0 < \gamma < 1$.

Preferably, another calculation method of CFcomp is as follows:

CFcomp is a parameter associated with the measured value of electrochemical impedance Z by the correlation $F_{comp}(Z;\Omega)$:

$$CFcomp = F_{comp}(Z;\Omega) = \Omega a \times \left(\frac{Z}{Z0}\right)^{\Omega b}$$

wherein, $\Omega$ is the built-in parameter array specific to the sensor $$\Omega = \begin{bmatrix} \Omega a \\ \Omega b \end{bmatrix},$$

and Z0 is the impedance value measured by the sensor in a controlled experimental environment;

when the user uses the finger blood glucose meter to detect the blood glucose value BG, the BG, the sensor current signal Is and CFcomp should conform to the following relationship with the smallest possible error:

$$BG = Is \times CFcomp = Is \times \Omega a \times (Z/Z0)^{\Omega b}$$

taking the natural logarithm of both ends of the equation and getting $$Ln(BG) = Ln[Is \times \Omega a \times (Z/Z0)^{\Omega b}] = Ln(Is) + Ln(\Omega a) + \Omega b \times Ln(Z/Z0)$$

letting the parameter matrix $$L_\Omega = \begin{bmatrix} \ln(\Omega a) \\ \Omega b \end{bmatrix}$$

step A, near each measurement time Tb of the finger blood glucose meter, screening out the dynamic blood glucose meter data whose time interval |Tb−Tz| is less than the threshold value, and extracting the following data:

1. BG: measured data of finger blood glucose meter
2. SG: blood glucose calculation data of dynamic glucose sensor
3. Is: current data of dynamic glucose sensor
4. Z: impedance data of dynamic glucose sensor
5. Tz: time stamp data of dynamic glucose sensor selecting the data with |SG−BG| less than the threshold value as valid samples to form a sample record package $[BG_n\ IS_n\ Z_n\ Tz_n]$ for calculation;

using the data in the last three months for regression, and arranging the subscript number n of the historical data variable in reverse order of Tz, that is, the closer to the current historical data, the smaller the subscript number, the data of the dynamic glucose sensor can come from multiple sensor probes of the same model;

step B, establishing sample matrix and weight matrix:

$$G = \begin{bmatrix} Ln(BG_1) - Ln(Is_1) \\ Ln(BG_2) - Ln(Is_2) \\ Ln(BG_3) - Ln(Is_3) \\ \vdots \\ Ln(BG_n) - Ln(Is_n) \end{bmatrix} \quad I = \begin{bmatrix} 1 & Ln(Z_1/Z0) \\ 1 & Ln(Z_2/Z0) \\ 1 & Ln(Z_3/Z0) \\ \vdots & \vdots \\ 1 & Ln(Z_n/Z0) \end{bmatrix}$$

$$W = \begin{bmatrix} w(Tz'_1) & & & & \\ & w(Tz'_2) & & & \\ & & w(Tz'_3) & & \\ & & & \ddots & \\ & & & & w(Tz'_n) \end{bmatrix}$$

wherein, $Tz'_n = Tcurrent - Tz_n$ the closer to the current time, the greater the weight is;

step C, solving the overdetermined equation $G = I(L_\Omega)$;

using the weighted least square method to solve the matrix equation $\widehat{L_\Omega} = (I^T W I)^{-1} I^T W G$;

step D, eliminating abnormal data: calculating the residual matrix $\hat{\varepsilon} = G - I\widehat{L_\Omega}$, removing the data items with residuals greater than the threshold value, and then repeating steps B to C to get the optimal solution $\widehat{L_\Omega}$; then calculating the $\Omega a$ from the value $Ln(\Omega a)$ obtained by the solution $\widehat{L_\Omega}$, and getting $$\hat{\Omega} = \begin{bmatrix} \Omega a \\ \Omega b \end{bmatrix}$$

step E, using the obtained $\hat{\Omega}$ to correct the current set $\Omega$ with a certain correction ratio $\gamma$:

$$\Omega := (1-\gamma) \times \Omega + \gamma \times \hat{\Omega}$$

the range of $\gamma$ values is $0 < \gamma < 1$.

An intelligent real-time dynamic blood glucose monitoring method based on cloud big data includes the following steps:

step 1: when the smart phone application detects that the implantable dynamic glucose sensor is connected with the smart phone and initiates operation, firstly, judging whether the user has a history of using the same type of implantable dynamic glucose sensor, if not, determining that the user is a new user, and initiating use of the conversion coefficient CF0 between the preset sensor signal Is and the blood glucose output value and the conversion coefficient change rate CFd, and uploading the data to cloud big data server. At the same time, outputting blood glucose monitoring value according to the preset conversion correlation through the implantable dynamic glucose sensor. If there is historical data of the user, determining that the user is an existing user, and downloading the records of the latest CF0 and CFd to the implantable dynamic glucose sensor from the cloud big data server through the smart phone as a parameter for calculating the sensor's blood glucose output value;

step 2: detecting whether the current time has reached a new measurement cycle through the implantable dynamic glucose sensor, if not, letting the system wait until entering a new measurement cycle, then, in each new measurement cycle, calculating the conversion coefficient CF (t) in the cycle, wherein t is the interval between the current timestamp Ts and the sensor start-up time T0s, wherein the operation in step 2 includes three input data points obtained from the sensor: sensor start-up time T0s, current timestamp Ts and Is (t), and may also contain the impedance measurement information Z obtained by the sensor in the current measurement cycle and parameters $\Omega$ and CFcal obtained or updated by the cloud big data server communication.

The process of calculating and outputting SG includes the following steps:

step A, firstly, checking whether there is newly acquired impedance measurement data Z in the current measurement cycle, if so, detecting the change of the impedance value from the last measurement and the update of CFcal. If there is no CFcal update recently and Z changes significantly, updating the compensation local conversion parameter CFcomp and uploading the impedance measurement data Z and timestamp Tz to the cloud big data server. If the change in Z is not significant, or CFcal is updated, only uploading the impedance measurement data Z and timestamp TZ, and using the current compensation conversion parameter CFcomp.

step B, checking whether the cloud big data server has newly acquired impedance compensation parameter $\Omega'$ and correction conversion parameter CFcal through smart phone in the current cycle; if yes, downloading updated $\Omega'$ and CFcal' from the cloud big data server through smart phone; if not, continuing to use current $\Omega$ and CFcal.

step C, calculating the current conversion coefficient CF(t), and the calculation formula is as follows:

$$CF(t) = \frac{CF0 + CFd \times t + \alpha \times CFcomp + \beta \times CFcal}{1 + \alpha + \beta}$$

wherein, $\alpha$, $\beta$ are the weight coefficients of CFcomp and CFcal respectively, and the value range is $0 < \alpha < 10$, $0 < \beta < 10$.

step D, obtaining the current signal Is (t) of the sensor and calculating the output blood glucose value SG (t) of the sensor, wherein the calculation formula is $SG(t) = Is(t) \times CF(t)$.

step 3: uploading the original output current signal value of the sensor, the calculated SG value, and the corresponding timestamp Ts to the cloud big data server through the smart phone.

step 4: when the smart phone receives the signal that the probe of the implantable dynamic glucose sensor reached the service life, informing the cloud computing module to calculate the new conversion coefficient CF0 and the conversion coefficient change rate CFd through a regression algorithm, and when the user uses the next new sensor probe, informing the dynamic glucose sensor to update the parameters through the smart phone in step 1.

step 5: when the user is using the implantable dynamic glucose sensor, if the user also uses the finger blood glucose meter for blood glucose measurement at the same time, uploading the measured blood glucose value BG and timestamp Tb to the cloud database through the smart phone.

step 6: when the cloud database receives the finger blood glucose meter data through the smart phone, informing the cloud computing module to calculate the new impedance compensation parameter $\Omega'$ and the correction conversion parameter CFcal' through the regression algorithm, and transferring the calculation results to the smart phone, then informing the implantable dynamic glucose sensor to update the parameters through the smart phone, so that the implantable dynamic glucose sensor can update the parameters in step 2.

The Beneficial Effects of the Invention are as Follows.

1. The invention provides a real-time dynamic blood glucose monitoring system including a smart phone and a cloud big data server, which can effectively correct the influence of individual differences of the user on the signal of the implanted sensor by accessing and processing historical blood glucose measurement data of the user stored in the cloud, so as to ensure the quality and accuracy of the measurement signal during operation of the sensor. This scheme is suitable for current electrochemical sensors containing oxidoreductase or redox pair media. The typical application can be an implantable glucose sensor for human subcutaneous tissue fluid containing glucose oxidase, but not limited to such applications.

2. The invention establishes a set of algorithms, by way of establishing a regression equation characteristic of the current signal, the electrochemical impedance measurement result and the user's historical blood glucose data, and solving the over determined equation group to compensate and modify the output result of the blood glucose value calculated by the dynamic blood glucose monitoring system, so as to improve the accuracy of the output result.

DETAILED DESCRIPTION OF THE EMBODIMENTS

The invention will be further explained in combination with the embodiment and the accompanying drawings. The following embodiments are only used to illustrate the invention, but not to limit the scope of implementation of the invention.

Figure 1:
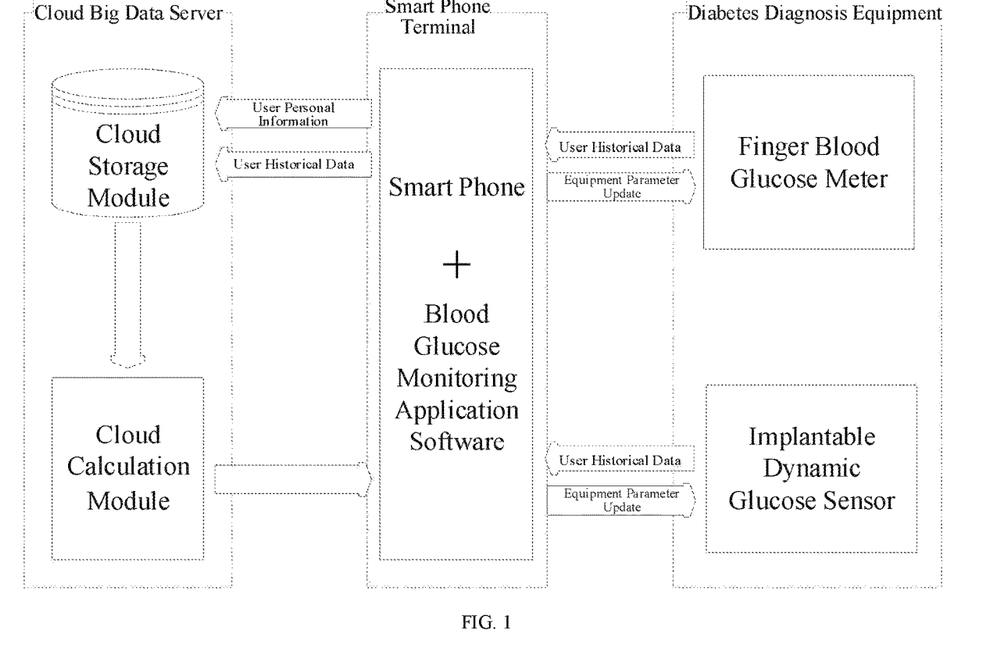
FIG. 1 is a schematic diagram of the system structure of the invention.

An intelligent real-time dynamic blood glucose monitoring system and method based on cloud big data is provided. As shown in FIG. 1, the system includes an implantable dynamic glucose sensor, a smart phone and a blood glucose monitoring application software installed on the smart phone, a finger blood glucose meter and a cloud big data server.

The glucose sensor includes a replaceable sensor probe, a reusable signal collector and a signal transmitter having an electrochemical impedance spectrum measurement function. The output of electrochemical impedance spectrum measurement includes the impedance value and phase or the real and imaginary parts of impedance. The frequency of electrochemical impedance measurement is less than the frequency of the glucose current signal measured by the sensor. The signal transmitter of the implantable dynamic glucose sensor is connected with the smart phone through a wireless connection such as Bluetooth communication, and transmits data with the blood glucose monitoring application software. In the connection and data transmission between the smart phone and the dynamic glucose sensor, the dynamic glucose sensor may only transmit the original current, impedance and time information. The calculation of blood glucose value and the storage of relevant parameters CF (t), CF0, CFd, CFcal and CFcomp, as well as the cloud data storage and updating, are realized in the smart phone application software, which may be a software as a service (SaaS).

The smart phone and the blood glucose monitoring application software installed on the smart phone have the functions of data transmission between the embedded glucose sensor and the finger blood glucose meter by way of wireless communication technology, as well as data uploading and downloading through the smart phone data network or wireless network and cloud big data server. Smart phones can also be other smart devices, such as a tablet, PC, laptop or the like.

The finger blood glucose meter has the function of collecting blood samples from a user's fingertips for blood glucose measurement, and can transmit data with the smart phone by way of wireless transmission;

The cloud big data server has the functions of storing, updating, calculating and transmitting the user's personal information and historical data. The user's personal information and historical data stored by the cloud big data server include, but are not limited to, the user's name, gender, age, contact number, serial number and related information of the user's implanted dynamic glucose sensor, original data Is of the sensor, signal to noise ratio (SNR), blood glucose output value SG and corresponding data measurement time and date Ts, conversion coefficient CF between sensor original data and blood glucose value and its related parameters, blood glucose value BG measured by user with the finger blood glucose meter and corresponding measurement time and date Tb, electrochemical impedance data measured by the implantable dynamic glucose sensor and corresponding measurement time and date Tz. The cloud big data server automatically corrects and calculates the parameter output data of the implantable dynamic glucose sensor and sends it to the smart phone terminal according to the user's historical data in the cloud database.

The conversion coefficient CF between the sensor raw data and the blood glucose value stored and calculated in the cloud big data server at time point t is calculated as follows $$CF(t) = \frac{CF0 + CFd \times t + \alpha \times CFcomp + \beta \times CFcal}{1 + \alpha + \beta}$$

wherein, time point t is the zero point when the sensor is started; CF0 is the initial value of conversion coefficient. CFd is the change rate of the conversion coefficient. CFcal is the correction compensation coefficient adjusted according to the blood glucose measurement value BG. CFcomp is the compensation conversion coefficient adjusted according to the electrochemical impedance data Z, which is calculated by the impedance measurement result Z and built-in compensation parameter array Ω. α, β are the weight coefficients of CFcomp and CFcal, the value range is $0<\alpha<10$, $0<\beta<10$.

The cloud big data server calculates the corresponding CF related parameters through the regression algorithm according to the real-time updated data and historical data of specific users.

CF0 and CFd are calculated as follows:

For each new user, the preset CF0 and CFd are used to calculate the sensor output blood glucose value:

$$SG = Is \times (CF0 + CFd \times t) = Is \times CF0 + t) \times CFd$$

After the user has used the finger blood glucose meter to measure and compare their own blood glucose, the measured value of the blood glucose meter is collected through the smart phone and uploaded to the cloud big data server, and the updated CF0 and CFd are calculated by regression equation. The specific method is as follows:

step A, extracting sample data: near each measurement time Tb of the finger blood glucose meter, screening out the dynamic glucose sensor data whose time interval |Tb−Ts| is less than the threshold value, and extracting the following data:
1. BG: measured data of finger blood glucose meter
2. SG: blood glucose calculation data of dynamic glucose sensor
3. Is: current data of dynamic glucose sensor
4. Ts: time stamp data of dynamic glucose sensor
5. T0s: start time stamp data of dynamic glucose sensor selecting the data with |SG−BG| less than the threshold value as valid samples to form a sample record package $[BG_n\ Is_n\ Ts_n\ T0s_n]$ for calculation; and using the data of the last three to six months for regression, and arranging the subscript number n of the historical data variable in reverse order of TS, that is, the closer to the current historical data, the smaller the subscript number, the data of dynamic glucose sensor can come from multiple sensor probes of the same model.

step B, establishing the sample matrix:

$$G = \begin{bmatrix} BG_1 \\ BG_2 \\ BG_3 \\ \vdots \\ BG_n \end{bmatrix} \quad I = \begin{bmatrix} Is_1 & Is_1 \times t_1 \\ Is_2 & Is_2 \times t_2 \\ Is_3 & Is_3 \times t_3 \\ \vdots & \vdots \\ Is_n & Is_n \times t_n \end{bmatrix}$$

wherein, $t_n = Ts_n - T0s_n$.

step C, establishing the coefficient matrix:

$$C = \begin{bmatrix} CF0 \\ CFd \end{bmatrix};$$

step D, constructing the weight matrix:

$$W = \begin{bmatrix} w(Ts'_1) & & & & \\ & w(Ts'_2) & & & \\ & & w(Ts'_3) & & \\ & & & \ddots & \\ & & & & w(Ts'_n) \end{bmatrix}$$

wherein, $Ts'_n = Tcurrent - Ts_n$, Tcurrent is the current time; $w(Ts'_n)$ is the weight coefficient of $Ts'_n$, so that the closer $Ts_n$ is to the current time, the greater its weight is. For example:

$$w = \begin{cases} 0.6 & Ts' \leq 1 \text{ month} \\ 0.3 & 1 \text{ month} < Ts' \leq 3 \text{ months} \\ 0.1 & 3 \text{ months} < Ts' \leq 6 \text{ months} \end{cases}$$

step E, solving the overdetermined equation G=IC:
using the weighted least square method to solve the matrix equation $\hat{C} = (I^T W I)^{-1} I^T W G$.

step F, eliminating abnormal data: calculating the residual matrix $\hat{\varepsilon} = G - I\hat{C}$, removing the data items with residuals greater than the threshold value, and then repeating step B to E of regression algorithm to obtain the sum of updated values $\widehat{CF0}$ and $\widehat{CFd}$ of CF0 and CFd.

step G, finally, using the obtained $\widehat{CF0}$ and $\widehat{CFd}$ calculated by regression to correct the current set CF0 and CFd with a certain correction ratio γ as the conversion coefficient setting of the next dynamic glucose sensor:

$$CF0 := (1-\gamma) \times CF0 + \gamma \times \widehat{CF0}$$

$$CFd := (1-\gamma) \times CFd + \gamma \times \widehat{CFd}$$

The range of γ values is 0<γ<1. For example, γ=0.6.

The calculation method of CFcal in the cloud big data server is as follows:

when the user uses the finger blood glucose meter to detect the blood glucose value BG, the BG, the sensor current signals Is and CFcal should conform to the following relationship with the smallest possible error:

$$BG = Is \times CFcal$$

step A, obtaining a new blood glucose value BG and measurement time Tb after each time the user uses the finger blood glucose meter for blood glucose detection, and selecting the dynamic glucose sensor data with time interval |Tb−Ts| less than the threshold value at the same time:
1. BG: measured data of finger blood glucose meter
2. SG: blood glucose calculation data of dynamic glucose sensor
3. Is: current data of dynamic glucose sensor
4. SNR: signal-to-noise ratio of dynamic glucose sensor current signal
5. Ts: time stamp data of dynamic glucose sensor selecting the data with |SG−BG| less than the threshold value as valid samples to form a sample record package $[BG_n\ Is_n\ SNR_n\ Ts_n]$ for calculation;

using the data in the latest period for regression, and arranging the subscript number n of the historical data variable in reverse order of TS, that is, the closer to the current historical data, the smaller the subscript number. All the dynamic glucose sensor data must come from the same sensor probe; wherein, the latest period includes the last 5 days, the latest 7 days, the last 10 days or the same period as the service life of the replaceable sensor probe;

step B, using regression algorithm to calculate the updated value CFcal' of CFcal:

$$CFcal' = \frac{\sum_{n=1}^{N} [Is_n \times BG_n \times SNR_n \times w(Ts'_n)]}{\sum_{n=1}^{N} [Is_n^2 \times SNR_n \times w(Ts'_n)]}$$

wherein, $Ts'_n = Tcurrent - Ts_n$, Tcurrent is the current time; $w(Ts'_n)$ is the weight coefficient of $Ts'_n$, so that the closer $Ts_n$ is to the current time, the greater its weight is. For example:

$$w(Ts'_n) = \begin{cases} 0.6 & t \leq 24 \text{ hours} \\ 0.3 & 24 \text{ hours} < t \leq 72 \text{ hours} \\ 0.1 & 72 \text{ hours} < t \leq 168 \text{ hours} \end{cases}$$

The calculation method of CFcomp is as follows:

CFcomp is a parameter associated with the measured value of electrochemical impedance Z by the correlation $F_{comp}(Z;\Omega)$:

$$CFcomp = F_{comp}(Z;\Omega) = \Omega a \times M(Z/Z0) + \Omega b$$

wherein, $\Omega$ is the built-in parameter array specific to the sensor $$\Omega = \begin{bmatrix} \Omega a \\ \Omega b \end{bmatrix}, M(Z/Z0)$$

is a function related to impedance data Z, and Z0 is the impedance value measured by the sensor in a controlled experimental environment. In this example, $M(Z/Z0)=e^{Z/Z0}$;

when the user uses the finger blood glucose meter to detect the blood glucose value BG, the BG, the sensor current signal Is and CFcomp should conform to the following relationship with the smallest possible error:

$$BG = Is \times CFcomp = Is \times M\left(\frac{Z}{Z0}\right) \times \Omega a + Is \times \Omega b = Is \times \Omega a \times e^{Z/Z0} + Is \times \Omega b$$

step A, near each measurement time Tb of the finger blood glucose meter, screening out the dynamic glucose sensor data whose time interval |Tb−Tz| is less than the threshold value, and extracting the following data:
  1. BG: measured data of finger blood glucose meter
  2. SG: blood glucose calculation data of dynamic glucose sensor
  3. Is: current data of dynamic glucose sensor
  4. Z: Impedance data of dynamic glucose sensor
  5. Tz: time stamp data of dynamic glucose sensor
selecting the data with |SG−BG| less than the threshold value as valid samples to form a sample record package $[BG_n\ IS_n\ Z_n\ Tz_n]$ for calculation;
using the data in the last three months for regression, and arranging the subscript number n of the historical data variable in reverse order of Tz, that is, the closer to the current historical data, the smaller the subscript number, the data of dynamic glucose sensor can come from multiple sensor probes of the same model;
step B, establishing sample matrix and weight matrix:

$$G = \begin{bmatrix} BG_1 \\ BG_2 \\ BG_3 \\ \vdots \\ BG_n \end{bmatrix} \quad I = \begin{bmatrix} Is_1 \times M(z_1/z0) & Is_1 \\ Is_2 \times M(z_2/z0) & Is_2 \\ Is_3 \times M(z_3/z0) & Is_3 \\ \vdots & \vdots \\ Is_n \times M(z_n/z0) & Is_n \end{bmatrix}$$

$$W = \begin{bmatrix} w(Tz'_1) & & & & \\ & w(Tz'_2) & & & \\ & & w(Tz'_3) & & \\ & & & \ddots & \\ & & & & w(Tz'_n) \end{bmatrix}$$

wherein, $Tz'_n = Tcurrent - Tz_n$
The closer $Tz_n$ is to the current time, the greater its weight is. For example, $$W = \begin{cases} 0.6 & Tz' \le 1 \text{ month} \\ 0.3 & 1 \text{ month} < Tz' \le 2 \text{ months} \\ 0.1 & 2 \text{ months} < Tz' \le 3 \text{ months} \end{cases}$$

step C, solving the overdetermined equation $G = I\Omega$;
using the weighted least square method to solve the matrix equation $\hat{\Omega} = (I^T W I)^{-1} I^T W G$;

step D, eliminating abnormal data: calculating the residual matrix $\hat{\varepsilon} = G - I\hat{\Omega}$, removing the data items with residuals greater than the threshold value, and then repeating steps B to C to get the optimal solution $\hat{\Omega}$;

step E, using the obtained $\hat{\Omega}$ to correct the current set $\Omega$ with a certain correction ratio $\gamma$:

$$\Omega := (1-\gamma) \times \Omega + \gamma \times \hat{\Omega}$$

The range of $\gamma$ values is $0 < \gamma < 1$. For example, $\gamma = 0.75$.
Another calculation method of CFcomp is as follows:
CFcomp is a parameter associated with the measured value of electrochemical impedance Z by the correlation $F_{comp}(Z;\Omega)$:

$$CFcomp = F_{comp}(Z;\Omega) = \Omega a \times \left(\frac{Z}{Z0}\right)^{\Omega b}$$

wherein, $\Omega$ is the built-in parameter array specific to the sensor $$\Omega = \begin{bmatrix} \Omega a \\ \Omega b \end{bmatrix},$$

and Z0 is the impedance value measured by the sensor in a controlled experimental environment;

when the user uses the finger blood glucose meter to detect the blood glucose value BG, the BG, the sensor current signal Is and CFcomp should conform to the following relationship with the smallest possible error:

$$BG = Is \times CFcomp = Is \times \Omega a \times (Z/Z0)^{\Omega b};$$

taking the natural logarithm of both ends of the equation and obtaining $$Ln(BG) = Ln[Is \times \Omega a \times (Z/Z0)^{\Omega b}] = Ln(Is) + Ln(\Omega a) + \Omega b \times Ln(Z/Z0)$$

letting the parameter matrix $$L_\Omega = \begin{bmatrix} \ln(\Omega a) \\ \Omega b \end{bmatrix}$$

step A, near each measurement time Tb of the finger blood glucose meter, screening out the dynamic blood glucose meter data whose time interval |Tb−Tz| is less than the threshold value, and extracting the following data:
  1. BG: measured data of finger blood glucose meter
  2. SG: blood glucose calculation data of dynamic glucose sensor
  3. Is: current data of dynamic glucose sensor
  4. Z: Impedance data of dynamic glucose sensor
  5. Tz: time stamp data of dynamic glucose sensor
selecting the data with |SG−BG| less than the threshold value as valid samples to form a sample record package $[BG_n\ IS_n\ Z_n\ Tz_n]$ for calculation;
using the data in the last three months for regression, and arranging the subscript number n of the historical data variable in reverse order of Tz, that is, the closer to the current historical data, the smaller the subscript number. The data of dynamic glucose sensor can come from multiple sensor probes of the same model;

step B, establishing sample matrix and weight matrix:

$$G = \begin{bmatrix} Ln(BG_1) - Ln(Is_1) \\ Ln(BG_2) - Ln(Is_2) \\ Ln(BG_3) - Ln(Is_3) \\ \vdots \\ Ln(BG_n) - Ln(Is_n) \end{bmatrix} \quad I = \begin{bmatrix} 1 & Ln(Z_1/Z0) \\ 1 & Ln(Z_2/Z0) \\ 1 & Ln(Z_3/Z0) \\ \vdots & \vdots \\ 1 & Ln(Z_n/Z0) \end{bmatrix}$$

$$W = \begin{bmatrix} w(Tz'_1) & & & & \\ & w(Tz'_2) & & & \\ & & w(Tz'_3) & & \\ & & & \ddots & \\ & & & & w(Tz'_n) \end{bmatrix}$$

wherein, $Tz'_n = Tcurrent - Tz_n$

The closer is to the current time, the greater its weight is;

step C, solving the overdetermined equation $G = I(L_\Omega)$;

using the weighted least square method to solve the matrix equation $\widehat{L_\Omega} = (I^T W I)^{-1} I^T W G$;

step D, eliminating abnormal data: calculating the residual matrix $\hat{\varepsilon} = G - I\widehat{L_\Omega}$, removing the data items with residuals greater than the threshold value, and then repeating steps B to C to get the optimal solution $\widehat{L_\Omega}$; then calculating the $\Omega a$ from the value $Ln(\Omega a)$ obtained by the solution $\widehat{L_\Omega}$, and obtaining $$\hat{\Omega} = \begin{bmatrix} \Omega a \\ \Omega b \end{bmatrix}$$

step E, using the obtained $\hat{\Omega}$ to correct the current set $\Omega$ with a certain correction ratio $\gamma$:

$$\Omega := (1-\gamma) \times \Omega + \gamma \times \hat{\Omega}$$

The range of $\gamma$ values is $0 < \gamma < 1$. For example, $\gamma = 0.5$.

Figure 2:
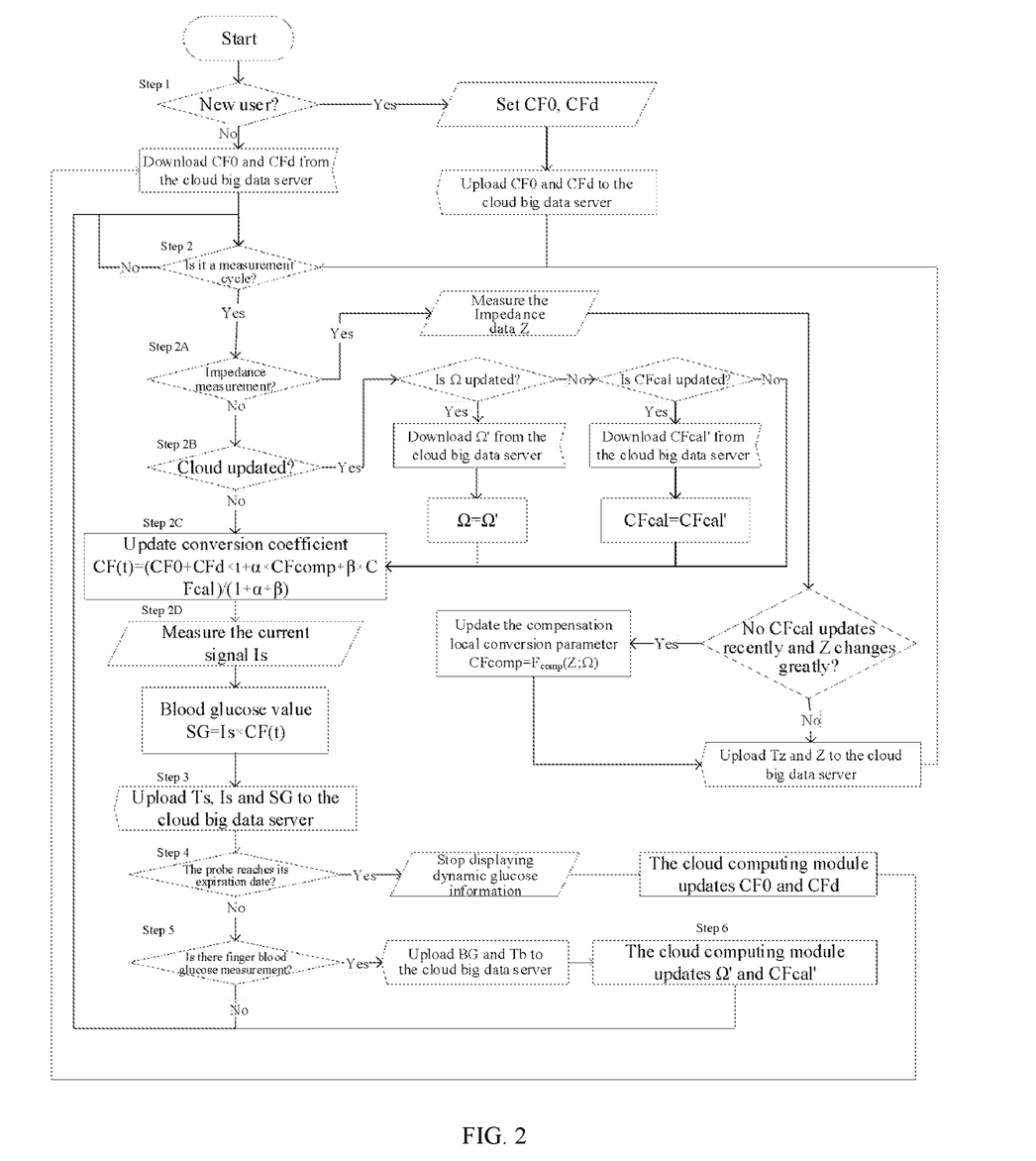
FIG. 2 is a flow diagram of the method of the invention.

An intelligent real-time dynamic blood glucose monitoring method based on cloud big data as shown in FIG. 2 includes the following steps:

step 1: when the smart phone application detects that the implantable dynamic glucose sensor is connected with the smart phone and begins operation, firstly judging whether the user has the history of using the same type of implantable dynamic glucose sensor. If not, determining that the user is a new user, and starting to use the conversion coefficient CF0 between the preset sensor signal Is and the blood glucose output value and the conversion coefficient change rate CFd, and uploading the data to the cloud big data server. At the same time, outputting the blood glucose monitoring value according to the preset conversion correlation through the glucose sensor. If there is historical data of the user, determining whether the user is an existing user, and downloading the records of the latest CF0 and CFd to the implantable dynamic glucose sensor from the cloud big data server through the smart phone as a parameter for calculating the sensor's blood glucose output value.

step 2: detecting whether the current time has reached a new measurement cycle through the implantable dynamic glucose sensor. If not, leaving the system idle until entering a new measurement cycle, then, in each new measurement cycle, calculating the conversion coefficient CF (t) in the cycle, in which t is the interval between the current timestamp Ts and the sensor start-up time T0s, wherein the operation in step 2 includes three input data points obtained from the sensor: sensor start-up time T0s; current timestamp Ts; and Is (t), and may also contain the impedance measurement information Z obtained by the sensor in the current measurement cycle and parameters $\Omega$ and CFcal obtained or updated by the cloud big data server communication.

The process of calculating and outputting SG includes the following steps:

step A, firstly, checking whether there is newly acquired impedance measurement data Z in the current measurement cycle. If so, detecting the change of the impedance value from the last measurement and the update of CFcal. If there is no CFcal update recently and Z changes significantly, updating the compensation local conversion parameter CFcomp and uploading the impedance measurement data Z and timestamp Tz to the cloud big data server. If the change in Z is not significant or if CFcal is updated, only uploading the impedance measurement data Z and timestamp TZ, and using the current compensation conversion parameter CFcomp;

step B, checking whether the cloud big data server has newly acquired impedance compensation parameter $\Omega'$ and correction conversion parameter CFcal through smart phone in the current cycle; if yes, downloading updated $\Omega'$ and CFcal' from the cloud big data server through smart phone; if not, continuing to use current $\Omega$ and CFcal;

step C, calculating the current conversion coefficient CF (t), and the calculation formula is as follows:

$$CF(t) = \frac{CF0 + CFd \times t + \alpha \times CFcomp + \beta \times CFcal}{1 + \alpha + \beta}$$

wherein, $\alpha$, $\beta$ are the weight coefficients of CFcomp and CFcal respectively, and the value range is $0 < \alpha < 10$, $0 < \beta < 10$;

step D, obtaining the current signal Is (t) of the sensor and calculating the output blood glucose value SG (t) of the sensor. The calculation formula is $SG(t) = Is(t) \times CF(t)$;

step 3: uploading the original output current signal value of the sensor, the calculated SG value, and the corresponding timestamp Ts to the cloud big data server through the smart phone;

step 4: when the smart phone receives the signal that the probe of the implantable glucose sensor reached the service life, informing the cloud computing module to calculate the new conversion coefficient CF0 and the conversion coefficient change rate CFd through the regression algorithm, and when the user uses the next new sensor probe, informing the dynamic glucose sensor to update the parameters through the smart phone in step 1;

step 5: when the user is using the implantable dynamic glucose sensor, if the user also uses the finger blood glucose meter for blood glucose measurement at the same time, uploading the measured blood glucose value BG and timestamp Tb to the cloud database through the smart phone;

step 6: when the cloud database receives the finger blood glucose meter data through the smart phone, informing the cloud computing module to calculate the new impedance compensation parameter $\Omega'$ and the correction conversion parameter CFcal' through the regression algorithm, and pushing the calculation results to the smart phone, then informing the implantable dynamic glucose sensor to update the parameters through the smart phone, so that the implantable dynamic glucose sensor can update the parameters in step 2.

What is claimed is:

1. An intelligent real-time dynamic blood glucose monitoring system based on cloud big data, comprising
an implantable dynamic glucose sensor,
a smart phone and a blood glucose monitoring application software installed on the smart phone,
a finger blood glucose meter and
a cloud big data server;
wherein the implantable dynamic glucose sensor comprises a replaceable sensor probe, a reusable signal collector configured to measure an electrochemical impedance spectrum- and transmit a signal, an output of the electrochemical impedance spectrum measurement comprises an impedance value and a phase or a real part and an imaginary part of an impedance; the signal transmitter of the implantable dynamic glucose sensor is connected with the smart phone through a wireless connection and transmits data with the blood glucose monitoring application software;
the smart phone and the blood glucose monitoring application software installed on the smart phone-is configured to transmit data with the implantable dynamic glucose sensor and the finger blood glucose meter through wireless communication technology, and upload data- and download data through a smart phone data network or a wireless network and the cloud big data server;
the finger blood glucose meter is configured to collect a blood sample from a user's fingertip for a blood glucose measurement, and transmit data with the smart phone through the wireless network;
the cloud big data server is configured to store, update, calculate and transmit personal information and historical data of the user, wherein the cloud big data server automatically corrects and calculates parameter output data of the implantable dynamic glucose sensor and sends the parameter output data to a terminal of the smart phone according to the historical data of the user in a cloud database, and wherein the cloud big data server calculates a conversion coefficient CF between original sensor data stored and the blood glucose value at a time point t as follows:

$$CF(t) = \frac{CF0 + CFd \times t + \alpha \times CFcomp + \beta \times CFcal}{1 + \alpha + \beta}$$

wherein, the time point t is a zero point when the implantable dynamic glucose sensor is started; CF0 is an initial value of the conversion coefficient CFd is a change rate of the conversion coefficient CFcal is a correction compensation coefficient adjusted according to the blood glucose measurement value BG; CFcomp is a compensation conversion coefficient adjusted according to an electrochemical impedance data Z; $\alpha$, $\beta$ are weight coefficients of the CFcomp and the CFcal, with a value range of $0<\alpha<10$, $0<\beta<10$;
according to real-time updated data and the historical data of the user, the cloud big data server calculates corresponding CF related parameters through a regression algorithm.

2. The intelligent real-time dynamic blood glucose monitoring system based on the cloud big data according to claim 1, wherein the personal information and the historical data stored in the cloud big data server of the user comprises user's name, gender, age, contact number, serial number and related information of the implantable dynamic glucose sensor, raw data Is of the implantable dynamic glucose sensor, signal-to-noise ratio SNR, blood glucose output value SG and measurement time and date Ts corresponding to the SG, a conversion coefficient CF and a related parameter between original data of the implantable dynamic glucose sensor and a blood glucose value, the blood glucose value BG measured by the finger blood glucose meter and measurement time and date Tb corresponding to the BG, electrochemical impedance data Z measured by the implantable dynamic glucose sensor and measurement time and date Tz corresponding to the Z.

3. The intelligent real-time dynamic blood glucose monitoring system based on the cloud big data according to claim 1, wherein the cloud big data server is configured to calculate the CF0 and the CFd as follows:
for each user, the cloud big data server is configured to calculate blood glucose value output by the implantable dynamic glucose sensor using a preset CF0 and CFd:

$$SG = Is \times (CF0 + CFd \times t) = Is \times CF0 + (Is \times t)CFd,$$

after the user has used the finger blood glucose meter to measure their own blood glucose, a measured value of the blood glucose meter is collected through the smart phone and uploaded to the cloud big data server, the cloud big data server is configured to calculate the updated CF0 and CFd by a regression equation, as follows:
step A, extract sample data: near each measurement time Tb of the finger blood glucose meter, screen out dynamic glucose sensor data having a time interval |Tb−Ts| less than a threshold value, and extract following data:
1. BG: measured data of the finger blood glucose meter
2. SG: blood glucose calculation data of the implantable dynamic glucose sensor
3. Is: current data of the implantable dynamic glucose sensor
4. Ts: time stamp data of the implantable dynamic glucose sensor
5. T0s: start time stamp data of the implantable dynamic glucose sensor
select data with |SG−BG| less than the threshold value as a valid sample to form a sample record package [$BG_n$ $Is_n$ $Ts_n$ $T0s_n$] for calculation;
use data of last three to six months for a regression, and arrange a subscript number n of a historical data variable in reverse order of TS, that is, the closer to current historical data, the smaller the subscript number, the data of the implantable dynamic glucose sensor come from multiple sensor probes of a same model;
step B, establish a sample matrix:

$$G = \begin{bmatrix} BG_1 \\ BG_2 \\ BG_3 \\ \vdots \\ BG_n \end{bmatrix}$$

$$I = \begin{bmatrix} Is_1 & Is_1 \times t_1 \\ Is_2 & Is_2 \times t_2 \\ Is_3 & Is_3 \times t_3 \\ \vdots & \vdots \\ Is_n & Is_n \times t_n \end{bmatrix}$$

wherein, $t_n = Ts_n - T0s_n$;

step C, establish a coefficient matrix:

$$C = \begin{bmatrix} CF0 \\ CFd \end{bmatrix};$$

step D, construct a weight matrix:

$$W = \begin{bmatrix} w(Ts'_1) & & & & \\ & w(Ts'_2) & & & \\ & & w(Ts'_3) & & \\ & & & \ddots & \\ & & & & w(Ts'_n) \end{bmatrix}$$

wherein, $Ts'_n = Tcurrent - Ts_n$, Tcurrent is a current time; $w(Ts'_n)$ is a weight coefficient of $Ts'_n$, so that the closer $Ts_n$ is to the current time, the greater the weight is;

step E, solve an overdetermined equation G=IC:
using a weighted least square method to solve a matrix equation $\hat{C} = (I^T W I)^{-1} I^T W G$;

step F, eliminate abnormal data: calculate a residual matrix $\hat{\varepsilon} = G - I\hat{C}$, remove data items with residuals greater than the threshold value, and then repeating step B to E of regression algorithm to obtain a sum of updated values $\widehat{CF0}$ and $\widehat{CFd}$ of CF0 and CFd;

step G, finally, use the updated values $\widehat{CF0}$ and $\widehat{CFd}$ calculated by regression to correct the CF0 and CFd with a predetermined correction ratio γ as a conversion coefficient setting of the next dynamic glucose sensor:

$$CF0 := (1-\gamma) \times CF0 + \gamma \times \widehat{CF0}$$

$$CFd := (1-\gamma) \times CFd + \gamma \times \widehat{CFd}$$

a range of γ values is 0<γ<1.

4. The intelligent real-time dynamic blood glucose monitoring system based on the cloud big data according to claim 1, wherein the cloud big data server calculates the CFcal as follows:

when the user uses the finger blood glucose meter to detect the blood glucose value BG, the BG, the current data of the dynamic glucose sensor Is and the CFcal conform to following relationship with a smallest possible error:

$$BG = Is \times CFcal$$

the cloud big data server is configured to: step A, obtain a new blood glucose value BG and measurement time Tb after each time the user uses the finger blood glucose meter for blood glucose detection, and select the dynamic glucose sensor data with a time interval |Tb−Ts| less than the threshold value at a same time:
1. BG: measured data of the finger blood glucose meter
2. SG: blood glucose calculation data of the implantable dynamic glucose sensor
3. Is: current data of the implantable dynamic glucose sensor
4. SNR: signal-to-noise ratio of a dynamic glucose sensor current signal
5. Ts: time stamp data of the implantable dynamic glucose sensor select the data with |SG−BG| less than the threshold value as the valid sample to form the sample record package $[BG_n, Is_n, SNR_n, Ts_n]$ for calculation;

using data in a latest period for regression, and arrange the subscript number n of the historical data variable in reverse order of TS, that is, the closer to the current historical data, the smaller the subscript number, all the dynamic glucose sensor data come from a same sensor probe; wherein, the latest period comprises last 5 days, latest 7 days, last 10 days or same period as a service life of the replaceable sensor probe;

step B, use the regression algorithm to calculate updated value CFcal' of CFcal:

$$CFcal' = \frac{\sum_{n=1}^{N}[Is_n \times BG_n \times SNR_n \times w(Ts'_n)]}{\sum_{n=1}^{N}[Is_n^2 \times SNR_n \times w(Ts'_n)]}$$

wherein, $Ts'_n = Tcurrent - Ts_n$, Tcurrent is the current time; $w(Ts'_n)$ is the weight coefficient of $Ts'_n$, so that the closer $Ts_n$ is to the current time, the greater its weight is.

5. The intelligent real-time dynamic blood glucose monitoring system based on the cloud big data according to claim 1, wherein the cloud big data server calculates the CFcomp as follows:

the CFcomp is a parameter associated with a measured value of the electrochemical impedance data Z by a correlation $F_{comp}(Z;\Omega)$:

$$CFcomp = F_{comp}(Z;\Omega) = \Omega a \times M(Z/Z0) + \Omega b$$

wherein, Ω is a built-in parameter array specific to the sensor $$\Omega = \begin{bmatrix} \Omega a \\ \Omega b \end{bmatrix}, M(Z/Z0)$$

is a function related to the electrochemical impedance data Z, and Z0 is the impedance value measured by the sensor in a controlled experimental environment;

when the user uses the finger blood glucose meter to detect the blood glucose value BG, the BG, the current data of the dynamic glucose sensor Is and the CFcomp conform to following relationship with a smallest possible error:

$$BG = Is \times CFcomp$$
$$= Is \times M(Z/Z0) \times \Omega a + Is \times \Omega b$$

the cloud big data server is configured to: step A, near each measurement time Tb of the finger blood glucose meter, screen out the implantable dynamic glucose sensor data having a time interval |Tb−Tz| less than the threshold value, and extract the following data:
1. BG: measured data of the finger blood glucose meter
2. SG: blood glucose calculation data of the implantable dynamic glucose sensor
3. Is: current data of the implantable dynamic glucose sensor
4. Z: Impedance data of the implantable dynamic glucose sensor
5. Tz: time stamp data of the implantable dynamic glucose sensor select the data with |SG−BG| less than the threshold value as valid samples to form the sample record package [$BG_n$ $IS_n$ $Z_n$ $Tz_n$] for calculation;

use the data in the last three months for a regression, and arranging the subscript number n of the historical data variable in reverse order of Tz, that is, the closer to the current historical data, the smaller the subscript number, the data of dynamic glucose sensor come from multiple sensor probes of the same model;

step B, establish a sample matrix and a weight matrix:

$$G = \begin{bmatrix} BG_1 \\ BG_2 \\ BG_3 \\ \vdots \\ BG_n \end{bmatrix}$$

$$I = \begin{bmatrix} Is_1 \times M(z_1/z0) & Is_1 \\ Is_2 \times M(z_2/z0) & Is_2 \\ Is_3 \times M(z_3/z0) & Is_3 \\ \vdots & \vdots \\ Is_n \times M(z_n/z0) & Is_n \end{bmatrix}$$

$$W = \begin{bmatrix} w(Tz'_1) & & & & \\ & w(Tz'_2) & & & \\ & & w(Tz'_3) & & \\ & & & \ddots & \\ & & & & w(Tz'_n) \end{bmatrix}$$

wherein, $Tz'_n = Tcurrent - Tz_n$ the closer $Tz_n$ is to the current time, the greater its weight is;

step C, solve an overdetermined equation $G = I\Omega$;

using a weighted least square method to solve a matrix equation $\hat{\Omega} = (I^T W I)^{-1} I^T W G$;

step D, eliminate abnormal data: calculating a residual matrix $\hat{\varepsilon} = G - I\hat{\Omega}$, removing data item with residuals greater than the threshold value, and then repeating steps B to C to get an optimal solution $\hat{\Omega}$;

step E, use the optimal solution $\hat{\Omega}$ to correct the current set $\Omega$ with a predetermined correction ratio $\gamma$:

$$\Omega := (1-\gamma) \times \Omega + \gamma \times \hat{\Omega}$$

a range of $\gamma$ values is $0 < \gamma < 1$.

6. The intelligent real-time dynamic blood glucose monitoring system based on the cloud big data according to claim 1, wherein the cloud big data server calculates the CFcomp as follows:

the Cfcomp is the parameter associated with a measured value of the electrochemical impedance data Z by a correlation $F_{comp}(Z; \Omega)$:

$$CFcomp = F_{comp}(Z; \Omega) = \Omega a \times \left(\frac{Z}{Z0}\right)^{\Omega b}$$

wherein, $\Omega$ is a built-in parameter array specific to the sensor $$\Omega = \begin{bmatrix} \Omega a \\ \Omega b \end{bmatrix},$$

and Z0 is the impedance value measured by the sensor in a controlled experimental environment;

when the user uses the finger blood glucose meter to detect the blood glucose value BG, the BG, the current data of the dynamic glucose sensor Is and Cfcomp conform to following relationship with a smallest possible error:

$$BG = Is \times Cfcomp = Is \times \Omega a \times (Z/Z0)^{\Omega b}$$

taking a natural logarithm of both ends of the equation and obtaining $$Ln(BG) = Ln[Is \times \varepsilon a \times (Z/Z0)^{\Omega b}] = Ln(Is) + Ln(\Omega a) + \Omega b \times Ln(Z/Z0)$$

letting the parameter matrix $$L_\Omega = \begin{bmatrix} \ln(\Omega a) \\ \Omega b \end{bmatrix}$$

the cloud big data server is configured to: step A, near each measurement time Tb of the finger blood glucose meter, screen out the implantable dynamic blood glucose meter data having a time interval |Tb−Tz| less than the threshold value, and extracting the following data:

1. BG: measured data of the finger blood glucose meter
2. SG: blood glucose calculation data of the implantable dynamic glucose sensor
3. Is: current data of the implantable dynamic glucose sensor
4. Z: impedance data of the implantable dynamic glucose sensor
5. Tz: time stamp data of the implantable dynamic glucose sensor select the data with |SG−BG| less than the threshold value as valid samples to form the sample record package [$BG_n$ $IS_n$ $Z_n$ $Tz_n$] for calculation;

use the data in the last three months for a regression, and arranging the subscript number n of the historical data variable in reverse order of Tz, that is, the closer to the current historical data, the smaller the subscript number, the data of dynamic glucose sensor come from multiple sensor probes of the same model;

step B, establish a sample matrix and a weight matrix:

$$G = \begin{bmatrix} Ln(BG_1) - Ln(Is_1) \\ Ln(BG_2) - Ln(Is_2) \\ Ln(BG_3) - Ln(Is_3) \\ \vdots \\ Ln(BG_n) - Ln(Is_n) \end{bmatrix}$$

$$I = \begin{bmatrix} 1 & Ln(Z_1/Z0) \\ 1 & Ln(Z_2/Z0) \\ 1 & Ln(Z_3/Z0) \\ \vdots & \vdots \\ 1 & Ln(Z_n/Z0) \end{bmatrix}$$

$$W = \begin{bmatrix} w(Tz'_1) & & & & \\ & w(Tz'_2) & & & \\ & & w(Tz'_3) & & \\ & & & \ddots & \\ & & & & w(Tz'_n) \end{bmatrix}$$

wherein, $Tz'_n = Tcurrent - Tz_n$ the closer $Tz_n$ is to the current time, the greater its weight is;

step C, solve an overdetermined equation $G=I(L_\Omega)$;

using a weighted least square method to solve a matrix equation $\widehat{L_\Omega} = (I_T WI)^{-1} I^T WG$;

step D, eliminate abnormal data: calculate a residual matrix $\hat{\varepsilon} = G - I\widehat{L_\Omega}$, remove data item with residuals greater than the threshold value, and then repeat steps B to C to get an optimal solution $\widehat{L_\Omega}$; then calculate the $\varepsilon\alpha$ from the value $Ln(\Omega\alpha)$ obtained by the optimal solution $\widehat{L_\Omega}$, and obtain $$\hat{\Omega} = \begin{bmatrix} \Omega a \\ \Omega b \end{bmatrix}$$

step E, use the optimal solution $\hat{\Omega}$ to correct the current set $\Omega$ with a predetermined correction ratio $\gamma$:

$$\Omega := (1-\gamma) \times \Omega + \gamma \times \hat{\Omega}$$

a range of $\gamma$ values is $0 < \gamma < 1$.

7. An intelligent real-time dynamic blood glucose monitoring method based on cloud big data, comprising the following steps:

step 1: when a smart phone application detects that an implantable dynamic glucose sensor is connected with the smart phone and starts to work, checking whether a user has a history of using a same type of the implantable dynamic glucose sensor;

wherein, when the user doesn't have the history of using the same type of the implantable dynamic glucose sensor, determining the user as a new user, using a conversion coefficient CF0 between a preset sensor signal Is and a blood glucose output value and a conversion coefficient change rate CFd, uploading data to a cloud big data server, and outputting a blood glucose monitoring value according to a preset conversion correlation through the implantable dynamic glucose sensor, wherein, when the user has the history of using the same type of the implantable dynamic glucose sensor, determining the user as an existing user, and downloading records of a latest CF0 and CFd of the user to the implantable dynamic glucose sensor from the cloud big data server through the smart phone as a parameter for calculating the blood glucose output value;

step 2: detecting whether a current time has reached a new measurement cycle through the implantable dynamic glucose sensor;

when the current time hasn't reached the new measurement cycle through the implantable dynamic glucose sensor, waiting until the system enters the new measurement cycle, then, in each new measurement cycle, calculating the conversion coefficient CF (t) in the new measurement cycle, wherein t is an interval between a current timestamp Ts and a sensor start-up time T0s, obtaining an impedance measurement data Z by the sensor in the current measurement cycle, and communicating with the cloud big data server to obtain updated parameters $\Omega$ and CFcal;

a process of calculating and outputting SG includes following steps:

step A, checking whether there is the newly acquired impedance measurement data Z in the current measurement cycle;

when there is the newly acquired impedance measurement data Z in the current measurement cycle, detecting a change of the impedance value from the last measurement and updating CFcal;

wherein, when there is no recent CFcal update and Z changes significantly, updating a compensation local conversion parameter CFcomp and uploading the impedance measurement data Z and timestamp Tz to the cloud big data server, wherein, when there is a recent CFcal update or there is no significant change in Z, uploading only the impedance measurement data Z and timestamp TZ, and using the current compensation conversion parameter CFcomp;

step B, checking whether the cloud big data server has newly acquired impedance compensation parameter $\Omega'$ and correction conversion parameter CFcal through the smart phone in the current cycle; if the cloud big data server has the newly acquired impedance compensation parameter $\Omega'$ and the correction conversion parameter CFcal through the smart phone in the current cycle, downloading updated $\Omega'$ and CFcal' from the cloud big data server through the smart phone; if the cloud big data server hasn't the newly acquired impedance compensation parameter $\Omega'$ and the correction conversion parameter CFcal through the smart phone in the current cycle, continuing to use current $\Omega$ and CFcal;

step C, calculating a current conversion coefficient CF (t), and a calculation formula for the CF (t) is as follows:

$$CF(t) = \frac{CF0 + CFd \times t + \alpha \times CFcomp + \beta \times CFcal}{1 + \alpha + \beta}$$

wherein, $\alpha$, $\beta$ are weight coefficients of CFcomp and CFcal, and a value range is $0 < \alpha < 10$, $0 < \beta < 10$;

step D, obtaining current data of the dynamic glucose sensor Is (t) and calculating an output blood glucose value SG (t) of the sensor, a calculation formula for the SG (t) is $SG(t) = Is(t) \times CF(t)$;

step 3: uploading an original output current signal value of the sensor, the calculated SG value, and the corresponding timestamp Ts to the cloud big data server through the smart phone;

step 4: when a smart phone receives a signal that a probe of the implantable dynamic glucose sensor reached a service life, informing a cloud computing module to calculate a new conversion coefficient CF0 and a new conversion coefficient change rate CFd through a regression algorithm, and when the user uses a next new sensor probe, informing the dynamic glucose sensor to update parameters through the smart phone in step 1;

step 5: when the user is using the implantable dynamic glucose sensor, if the user also uses the finger blood glucose meter for blood glucose measurement at the same time, uploading the measured blood glucose value BG and timestamp Tb to a cloud database through the smart phone;

step 6: when the cloud database receives finger blood glucose meter data through the smart phone, informing the cloud computing module to calculate a new impedance compensation parameter $\Omega'$ and a new correction conversion parameter $CFcal'$ through the regression algorithm, and pushing calculation results to the smart phone, then informing the implantable dynamic glucose sensor to update the parameters through the smart phone, so that the implantable dynamic glucose sensor updates the parameters in step 2.

\* \* \* \* \*